United States Patent [19]
Honeycutt et al.

[11] Patent Number: 5,885,907
[45] Date of Patent: Mar. 23, 1999

[54] METHOD OF DISPOSAL OF HOT WATER SOLUBLE GARMENTS AND LIKE FABRICS

[75] Inventors: Travis W. Honeycutt, Gainesville; Baosheng Lee, Duluth, both of Ga.

[73] Assignee: Isolyser Company, Inc., Norcross, Ga.

[21] Appl. No.: 963,990

[22] Filed: Nov. 4, 1997

Related U.S. Application Data

[63] Continuation of Ser. No. 708,841, Sep. 9, 1996, abandoned, which is a continuation-in-part of Ser. No. 286,814, Aug. 5, 1994, Pat. No. 5,620,786, which is a continuation of Ser. No. 55,083, Apr. 29, 1993, abandoned.

[51] Int. Cl.$^6$ .................................................. D04H 1/00
[52] U.S. Cl. ........................ 442/50; 264/185; 442/401; 442/402; 442/409; 442/417; 442/365
[58] Field of Search ............................. 442/50, 401, 402, 442/409, 417, 365; 264/185

[56] References Cited

U.S. PATENT DOCUMENTS

| | | |
|---|---|---|
| 2,340,866 | 2/1944 | Danglemaier . |
| 2,395,616 | 2/1946 | Dangelmaier . |
| 2,408,377 | 10/1946 | Dangelmaier . |
| 2,430,949 | 11/1947 | Porter et al. . |
| 2,909,502 | 10/1959 | Matsumoto et al. . |
| 3,089,493 | 5/1963 | Calindo . |
| 3,314,809 | 4/1967 | Nlug . |
| 3,372,311 | 3/1968 | Lubur . |
| 3,413,229 | 11/1968 | Bianco et al. . |
| 3,484,874 | 12/1969 | Bichenheuser . |
| 3,578,619 | 5/1971 | Reeder . |
| 3,607,812 | 9/1971 | Takigawa et al. . |
| 3,637,657 | 1/1972 | Moril et al. . |
| 3,762,454 | 10/1973 | Wilhens . |
| 3,790,067 | 2/1974 | Scheier . |
| 3,859,125 | 1/1975 | Miller et al. . |
| 3,865,918 | 2/1975 | Mitchell et al. . |
| 3,886,112 | 5/1975 | Watson et al. . |
| 3,886,610 | 6/1975 | Shelden . |
| 3,930,086 | 12/1975 | Harmon ................................ 428/131 |
| 3,931,088 | 1/1976 | Sakurada et al. . |
| 4,073,733 | 2/1978 | Yamauchi et al. . |
| 4,079,036 | 3/1978 | Ohmori et al. . |
| 4,258,849 | 3/1981 | Miller ..................................... 206/812 |
| 4,279,752 | 7/1981 | Sueoka et al. . |
| 4,295,850 | 10/1981 | Haberli et al. . |
| 4,343,133 | 8/1982 | Daniels et al. . |
| 4,478,971 | 10/1984 | Ballard . |
| 4,612,157 | 9/1986 | Genba et al. ........................... 204/185 |
| 4,620,999 | 11/1986 | Holmes . |
| 4,651,725 | 3/1987 | Kifune et al. . |
| 4,952,550 | 8/1990 | Wallach et al. . |
| 4,959,341 | 9/1990 | Wallach . |
| 4,959,464 | 9/1990 | Yeh . |
| 4,971,861 | 11/1990 | Watanabe et al. ...................... 428/364 |
| 5,051,222 | 9/1991 | Marten et al. . |
| 5,106,890 | 4/1992 | Maruhashi et al. . |
| 5,181,966 | 1/1993 | Honeycutt et al. . |
| 5,181,967 | 1/1993 | Honeycutt . |
| 5,183,571 | 2/1993 | Hanel et al. . |
| 5,207,837 | 5/1993 | Honeycutt . |
| 5,208,104 | 5/1993 | Ueda et al. ............................. 428/364 |
| 5,225,120 | 7/1993 | Graiver et al. . |
| 5,268,222 | 12/1993 | Honeycutt .............................. 428/224 |

FOREIGN PATENT DOCUMENTS

| | | |
|---|---|---|
| 8902229 | 1/1990 | Brazil . |
| 0050288 | 10/1981 | European Pat. Off. . |
| 0107576 | 5/1984 | European Pat. Off. . |
| 0176316 | 4/1986 | European Pat. Off. . |
| 0272816 | 6/1988 | European Pat. Off. . |
| 1519530 | 4/1970 | Germany . |
| 3017246 | 11/1981 | Germany . |
| 47-41741 | 10/1972 | Japan . |
| 55-71532 | 5/1980 | Japan . |
| 59-100704 | 6/1984 | Japan . |
| 60-44897 | 3/1985 | Japan . |
| 61-159995 | 7/1986 | Japan . |
| 2-68396 | 3/1990 | Japan . |
| 386161 | 1/1933 | United Kingdom . |
| 743165 | 1/1956 | United Kingdom . |
| 1187690 | 4/1970 | United Kingdom . |
| 1374199 | 11/1974 | United Kingdom . |
| 1451619 | 10/1976 | United Kingdom . |
| 2102461 | 2/1983 | United Kingdom . |
| 2119709 | 11/1983 | United Kingdom . |
| 2211088 | 6/1989 | United Kingdom . |
| 2211196 | 6/1989 | United Kingdom . |
| 2248842 | 4/1992 | United Kingdom . |
| WO9114413 | 10/1991 | WIPO . |
| WO9117210 | 11/1991 | WIPO . |

*Primary Examiner*—James J. Bell
*Attorney, Agent, or Firm*—Needle & Rosenberg, P.C.

[57] ABSTRACT

A towel, sponge and gauze made from a plurality of fibers of polyvinyl alcohol that are only water soluble at temperatures above 37° C. The polyvinyl alcohol fibers have a degree of hydrolysis of at least 80% with a degree of polymerization between approximately 300 to 3000.

16 Claims, No Drawings

METHOD OF DISPOSAL OF HOT WATER SOLUBLE GARMENTS AND LIKE FABRICS

RELATED APPLICATION

This is a continuation of Ser. No. 08/708,841, filed Sep. 9, 1996 abandoned, which is a continuation-in-part, of application Ser. No. 08/286,814 filed Aug. 5, 1994, now U.S. Pat. No. 5,620,786 which is a continuation of 08/055,083 filed Apr. 29, 1993 abandoned.

FIELD OF INVENTION

The present invention deals with specific products, namely, towels, sponges and gauzes which are produced from selectively hot water soluble polyvinyl alcohol resins. The resins are configured into fibers which are, in turn, used to construct the subject finished products.

BACKGROUND OF THE INVENTION

Hospital patient care generates considerable quantities of infectious medical waste in primary and acute care facilities. There has been a general conversion from reusable, cleanable items to disposable items over the last three decades. These conversions were made to promote antiseptic techniques in patient care and to decrease the potential for cross-infections between patients, staff and the general public. Recent federal and state government regulations such as the Medical Waste Tracking Act of 1988 and OSHA Medical Facility rules have resulted in a substantial increase in medical waste that must be classified as "infectious."

When a patient is admitted to the hospital, the patient produces approximately 55 pounds of medical waste per day. Approximately 20% of this waste is infectious. The current stated objective of the American Hospital Association and the Centers for Disease Control is to treat medical waste as soon as it is generated. Both organizations recognize that medical waste is primarily an occupational hazard for health care workers and not an environmental problem. The best way to handle infectious medical waste is to disinfect it at the point of generation and dispose of the treated medical waste with a minimum on premises handling and storage. The need for an effective way to dispose of medical waste has been highlighted by the amendment made to 29 CFR 1910.1030 which provides for the federal regulation under the Occupational Safety and Health Act, 29 USC 655, 657 to control blood borne pathogens. Specifically, the Act calls for the establishment of an exposure control plan, the containment of specimens of blood or other potentially infectious materials and the general tightening of precautionary measures to minimize the spread of disease. A safe and effective way to dispose of hospital waste would greatly facilitate compliance with the above-referenced Act.

As a result, consumption of medical disposable woven or non-woven products has been growing at a rate of approximately 10% a year. In 1988, sales totaled approximately 1.155 billion dollars. It is projected that as of the end of 1996, sales of medical disposable non-woven products will have exceeded two and a half billion dollars. In the United States, there are at least 30 million surgical procedures performed each year. After each surgical procedure, it is necessary that the operating theater be disinfected before a new procedure is performed to minimize any exposure the patients may bring to other patients or staff. This is particularly important in light of today's increasingly stringent regulations regarding occupational exposure to blood and bodily fluids.

Towels, sponges and gauzes have been in use since the first days of surgical procedures. They are used either to manipulate tissue, absorb blood and other oxidants of the wound site, as well as being useful to cleanse hands and assist in cleansing certain utensils used in various surgical procedures. Traditionally, towels, sponges and gauzes have been made from cotton fibers, though in recent years attempts have been made to provide replacements from other fibers including polyesters, rayons and other staple materials. These fibers were chosen because of their relative availability and cleanliness as man-made materials. Cotton is an agricultural material with volatile price and availability fluctuations. It has been noted that cotton replacements have, by and large, been unsatisfactory although many attempts have been made to mimic the appearance of cotton, all of which have been in vain.

Hospitals generally discard gauzes, sponges and towels after surgical use. Disposal takes place in either a landfill or by incineration. However, in either case, the handling of articles after use promotes the exposure of certain blood borne diseases to those employees who are charged with the responsibility for bagging and introducing such materials into the disposal process.

It is thus an object of the present invention to provide suitable towels, sponges and gauze capable of being disposed of after use while avoiding additional burdens being placed upon landfills and other disposal sites.

It is yet a further object of the present invention to provide suitable towels, sponges and gauze which, after use, can be solubilized and substantially sterilized in a single operation.

These and further objects will be more readily appreciated when considering the following disclosure and dependent claims.

SUMMARY OF THE INVENTION

The present invention provides an article comprising a member selected from the group consisting of towels, sponges and gauzes comprising a plurality of fibers of polyvinyl alcohol that are only water soluble at temperatures above about 37° C.

In a further embodiment, the present invention provides an article comprising a member selected from the group consisting of towels, sponges and gauzes comprising a plurality of fibers of crystallized polyvinyl alcohol that is water soluble at temperatures only above about 37° C., wherein the polyvinyl alcohol fibers are produced by dope extrusion and treatment with heat and stretching of a greater than 98% saponified polyvinyl acetate and the degree of polymerization for the fibers is from about 1300 to about 2000.

In yet another embodiment, the present invention provides an article comprising a member selected from the group consisting of towels, sponges and gauzes comprising a plurality of fibers of crystallized polyvinyl alcohol that is water soluble at temperatures only above about 37° C., including an effective amount of an anti-blocking agent, and an effective amount of a wetting agent, wherein the polyvinyl alcohol fibers are produced by dope extrusion and treatment with heat and stretching of a greater than 98% saponified polyvinyl acetate and the degree of polymerization for the fibers is from about 1300 to about 2000.

In another embodiment, the present invention provides an article comprising a member selected from the group consisting of towels, sponges and gauzes comprising a plurality of fibers of crystallized polyvinyl alcohol that is water soluble at temperatures only above about 37° C., including an effective amount of an anti-blocking agent and an effective amount of a wetting agent.

In another embodiment, the present invention provides a method of disposing of an article comprising a member selected from the group consisting of towels, sponges and gauzes comprised of a plurality of fibers of polyvinyl alcohol that are only water soluble at temperatures above about 37° C., the method comprising contacting the article comprising a member selected from the group consisting of towels, sponges and gauzes with water having a temperature above about 37° C. for a period of time sufficient to dissolve the article in water.

DETAILED DESCRIPTION OF THE INVENTION

The present invention fulfills the needs of hospitals and health care facilities by providing disposable towels, sponges and gauzes while teaching methods of their disposal after use. The articles are made up from a fabric that is comprised of fibers of polyvinyl alcohol which are water soluble at temperatures above approximately about 37° C., preferably above about 50° C., more preferably above about 70° C., and even more preferably above about 90° C. For articles having dissolution temperatures of 70° C. to 90° C. and above, the polyvinyl alcohol fibers are produced by a process of dope extrusion (also referred to as "wet spinning", "solution spinning" or "wet/solution spinning") and then treated with heat and stretching. Alternatively, such articles may be produced by melt spinning or hydrogel spinning following by heating and stretching. For articles having dissolution temperatures of from about 37° C. to 70° C., the fibers are produced by either melt spinning or hydrogel spinning following by heating and stretching as described herein.

In particular, in one embodiment, the present invention provides towels, sponges and gauzes comprising a plurality of fibers comprised of polyvinyl alcohol that are only water soluble at temperatures above about 37° C. In a further embodiment, the polyvinyl alcohol comprises crystallized polyvinyl alcohol. In yet another embodiment, the fibers are produced by dope extrusion and treatment with heat and stretching. In an alternate embodiment, the fibers are produced by melt extrusion (or "melt spinning") and treatment with heat and stretching. In yet another alternate embodiment, the fibers are produced by hydrogel extrusion (or "hydrogel extrusion") and treatment with heat and stretching.

In a further embodiment, the polyvinyl alcohol is produced from a greater than 80% saponified polyvinyl acetate. In yet another embodiment, the polyvinyl alcohol is produced from a greater than 98% saponified polyvinyl acetate. In a further embodiment, the polyvinyl alcohol is produced from a greater than 99% saponified polyvinyl acetate. In an alternate embodiment, the degree of polymerization of the fibers is from about 300 to about 3000. In a further embodiment, the degree of polymerization of the fibers is from about 700 to about 2000. In yet another further embodiment, the degree of polymerization of fibers is from about 1300 to about 2000.

Moreover, the present invention provides the towels, sponges and gauzes as described above wherein the water content of the fibers is maintained at from about 1.5 to about 15.0% by weight.

In a further embodiment, the present invention provides towels, sponges and gauzes as described above further comprising from about 0.1 to about 5.0% by weight of an anti-blocking agent. In another embodiment, the present invention provides towels, sponges and gauzes as described above wherein the fibers are yarn spun, thermally bonded, chemically bonded, needle punched, wet laid or air laid.

In an alternate embodiment, the present invention provides the above-described towels, sponges and gauzes, further comprising from about 0.1 to about 2.0% by weight of a wetting agent.

In a further embodiment of the present invention, the polyvinyl alcohol has a degree of crystallinity of at least about 0.20. In a further embodiment, the polyvinyl alcohol has a degree of crystallinity of at least about 0.40. In yet a further embodiment, the polyvinyl alcohol has a degree of crystallinity of at least about 0.70. Moreover, in a further embodiment, the polyvinyl alcohol has a degree of orientation of at least about 0.20. In a further embodiment, the polyvinyl alcohol has a degree of orientation of at least about 0.40. In yet a further embodiment, the polyvinyl alcohol has a degree of orientation of at least about 0.50.

In yet a further embodiment of the present invention, the polyvinyl alcohol is only water soluble at temperatures above about 50° C. In another preferred embodiment, the polyvinyl alcohol is only water soluble at temperatures above about 70° C. In a more preferable embodiment, the polyvinyl alcohol is only water soluble at temperatures above about 90° C.

In an alternate embodiment, the present invention provides towels, sponges and gauzes comprising a plurality of fibers comprising crystallized polyvinyl alcohol that is water soluble at temperatures only above about 37° C., and wherein the polyvinyl alcohol fibers are produced by dope extrusion and treatment with heat and stretching of a greater than 98% saponified polyvinyl acetate and the degree of polymerization for the fibers is from about 1300 to about 2000.

In yet another embodiment, the present invention provides towels, sponges and gauzes comprising a plurality of fibers comprising crystallized polyvinyl alcohol that is water soluble at temperatures only above about 37° C., including an effective amount of an anti-blocking agent, and an effective amount of a wetting agent, wherein the polyvinyl alcohol fibers are produced by dope extrusion and treatment with heat and stretching of a greater than 98% saponified polyvinyl acetate and the degree of polymerization for the fibers is from about 1300 to about 2000.

In a further embodiment, the present invention provides a towel, sponge or gauze comprising a plurality of fibers comprising crystallized polyvinyl alcohol that is water soluble at temperatures only above about 37° C., wherein the fibers are formed into a towel, sponge or gauze, including an effective amount of an anti-blocking agent, and an effective amount of a wetting agent. In an alternate preferred embodiment, the polyvinyl alcohol fibers are produced by dope extrusion and treatment with heat and stretching of a greater than 98% saponified polyvinyl acetate. In yet another alternate embodiment, the degree of polymerization for the fibers is from about 1300 to about 2000. In yet another embodiment, the water content of the fibers is maintained at from about 1.5 to about 15% by weight.

In addition, the present invention provides a method of disposing of towels, sponges and gauzes comprised of a plurality of fibers of polyvinyl alcohol that are only water soluble at temperatures above about 37° C., the method comprising contacting the fibers with water having a temperature above about 37° C. for a period of time sufficient to dissolve the fibers in the water.

The fibers may be prepared by wet/solution spinning ("dope extrusion"), melt spinning or hydrogel spinning. The particular process used depends upon the desired dissolution temperature of the polyvinyl alcohol fibers. For instance, producing fibers having dissolution temperature of 70° C. and above is preferably accomplished by using a hydrolyzed polyvinyl acetate with a percentage of hydrolysis of at least about 98% and is preferably accomplished using any of the three processes listed above. Alternatively, producing fibers having dissolution temperatures of from about 37° C. to about 70° is preferably accomplished by using a hydrolyzed polyvinyl acetate with a percentage of hydrolysis of at least about 80% to about 98% using the melt spinning or hydrogel spinning processes. In one embodiment, postdrawing and heat annealing may be used to increase the degrees of crystallization and orientation of the polyvinyl alcohol, resulting in an increased dissolution temperature for the end product polyvinyl alcohol fibers.

Polyvinyl alcohol fibers having a solubilization temperature of about 93° C. are preferred for hot water solubility applications. Such fibers are commercially available (Japan Kurary, "vinylon" product) or may be made using the following process.

In a preferred embodiment, polyvinyl alcohol fibers soluble at from 70° C. to about 93° C. (or higher) are prepared by dope extrusion as follows. Ray polyvinyl alcohol is washed in deionized water several times. The polyvinyl alcohol is then dissolved in hot water of approximately 100° C. to make a polyvinyl alcohol solution of from about 10 to about 25% concentration. The solution is preferably filtered and degassed.

The filtered and degassed solution is pumped through fine holes of a spinneret and into a supersaturated $Na_2SO_4$ solution (Glauber's salt) is at 40° C. to about 50° C. For improving the fiber strength, a suitable stretching treatment is given prior to heat treatment. For instance, the filament can be wet drawn to about 2.4 times its original length in a further supersaturated $Na_2SO_4$ solution. The filament is then dried and drawn again to a total stretching of about 3 times (for solubility closer to 70° C.) to 6 times (for solubility closer to 90° C.) its original length, with heating at from 200° to about 250° C., preferably at about 220° C. At this point, the filaments are cut to length, crimped in a 70° C. supersaturated $Na_2SO_4$ solution and washed in room temperature deionized water. The resulting filament is then further processed in an oiling step where surfactants such as lubricants, anti-static agents and cohesion agents are added. Finally, the fibers are tumble dried, in air, until thoroughly dry. These fibers are then optionally wound for subsequent use in manufacturing the towels, sponges and gauzes of the present invention.

For the purposes of the present invention, suitable anti-static agents are any known in the art that can be used with polyvinyl alcohol fibers. They include, but are not limited to, a mixture of polyethylene oxide (POE) alkylethersulfate sodium $[RO(CH_2CH_2))_nSO_3Na]$ and alkyl phosphate potassium: $[(RO)_2P(O)(OK)]$ or $[(RO)P(O)(OK)_2]$. Moreover, for the present invention, suitable cohesion agents can be used with polyvinyl alcohol fibers and include, but are not limited to, POE alkyl ether. Finally, suitable anti-friction ("lubricants") agents can be employed and include any known in the art that can be used with polyvinyl alcohol fibers such as, but not limited to, glyceryl stearate: $C_{17}H_{35}C(O)OCH_2C(H)(OH)CH_2OH$. As such combinations of these additives can be employed, for example, the agents can be used in an 80% anti-static, 10% anti-friction, and 10% cohesion mixture which may be diluted in water to about 50/50. This mixture can then be used to produce an about 0.21% final finishing level.

It should be noted that the water dissolution temperature of polyvinyl alcohol fibers is increased by heat treatment, so long as the original hydrolyzed polyvinyl acetate possesses a sufficient percentage of hydrolysis. Thus, hot water insolubility of over 90° C. calls for the use of greater than 98% hydrolyzed polyvinyl acetate. However, lower solubility temperatures can be achieved with lower hydrolysis percentages, ie. closer to 80% hydrolysis as specified elsewhere herein. As such, the polyvinyl alcohol fibers will not dissolve at room temperature but will in water at temperatures higher than 37°, preferably 70° C., more preferably 80° C., more preferably still at 90° C., an even more preferably 93° C.

In an alternate embodiment, polyvinyl alcohol fibers soluble at from 37° C. to about 70° C. are prepared by melt spinning. For melt spinning, the polyvinyl alcohol is mixed with a plasticizer, such as glycerine polyglycol. Then, at a temperature of between about 190° to about 220° C., the mixture is melted, mixed and spun through a spinneret. Heating and stretching occurs as described above for the wet spinning process. The polyvinyl alcohol for this melt spinning process is preferably produced from a 80–98% saponified polyvinyl acetate, so as to ensure solubility of between 37° C. and 70° C.

In a further alternate embodiment, polyvinyl alcohol fibers soluble at from 37° C. to about 70° C. are prepared by hydrogel spinning. For hydrogel spinning, the polyvinyl alcohol is mixed with water and, at a temperature of between about 90° to about 100° C., the mixture is melted and spun through a spinneret. Heating and stretching occurs as described above for the wet spinning process. The polyvinyl alcohol for this hydrogel spinning process is preferably produced from a 80–98% saponified polyvinyl acetate, so as to ensure solubility of between 37° C. and 70° C.

The polyvinyl alcohol useful for the present invention is preferably of a crystallized nature. In one embodiment, the degree of crystallinity is at least 0.20, in another embodiment at least 0.25, in another embodiment at least 0.30, in another embodiment at least 0.35, in another embodiment at least 0.40, in another embodiment at least 0.50, in another embodiment at least 0.60, in another embodiment at least 0.70, in another embodiment at least 0.80, in another embodiment at least 0.90 and in another embodiment at least 0.95. In a further embodiment, the degree of orientation for the heated and stretched polyvinyl alcohol fibers is at least 0.20, in another embodiment at least 0.40, in another embodiment at least 0.50, in another embodiment at least 0.60, in another embodiment at least 0.70, in another embodiment at least 0.80, in another embodiment at least 0.90, and in another embodiment at least 0.95. The degree of crystallinity and the degree of orientation are measured by IR spectroscopy. The degree of crystallinity is the ratio of crystalline area to amorphous area. The degree of orientation is the ratio of non-oriented area to oriented.

The water content of polyvinyl alcohol is preferably kept at a value between approximately 1.5 to 15.0% (wt.), preferably 5% (wt.). The polyvinyl alcohol is further characterized as having a degree of polymerization between approximately 300 to 3000, preferably of from 700 to 2000, more preferably from about 1300 to about 2000, and most preferably about 1700. In an alternate preferred embodiment, to achieve hot water solubility of closer to 70° C., it is desirable to use polyvinyl alcohol characterized as having a degree of polymerization of below about 1000.

In addition, the polyvinyl alcohol is produced from greater than at least about 80%, more preferably at least about 90%, even more preferably at least about 95%, even more preferably at least about 98%, even more preferably 99%, and even more preferably 99.5% or greater saponified polyvinyl acetate.

As noted, in one preferred embodiment, the present invention provides for novel towels, sponges and gauzes and their method of disposal for use primarily in the medical industry in hospitals, out-patient facilities and home environments. At such facilities, such products generally come into contact with human bodily fluids such that disposal and disinfection has become a matter of major concern in light of the lack of biodegradability of prior products and the potential spread of human fluid-borne diseases such as hepatitis B and AIDS. In order to cope with these difficulties, it is proposed that suitable towels, sponges and gauzes be composed of fabric produced from fibers comprising polyvinyl alcohol which are water soluble at temperatures preferably above 37° C., and more preferably above 50° C. If these products were soluble at significantly lower temperatures (e.g., below 37° C.), inadvertent solubilization would occur in the even that they were to contact certain fluids near human body temperature, such as human blood or urine. Polyvinyl alcohol which dissolves only at higher temperatures such as above 37° C., more preferably 50° C., even more preferably above 70° C., and even more preferably above 90° C. prevents inadvertent solubilization and provides a preferable material for practicing the present invention. In fact, it is contemplated that disposal in a hot water bath, such as a washing machine at or near the boiling point of water dedicated solely to solubilizing the products of this invention as well as similar films, fibers and garments, would also be an effective disinfecting media. However, lower temperature disinfecting media are specifically contemplated so long as their temperature is above the dissolution temperature of the polyvinyl alcohol fibers. Two objectives would thus be accomplished, namely, that the polymer would be both disinfected and would also be solubilized for disposal through the sewer system. Not only would this lessen the burden now being imposed upon current landfill sites, but liquid sewer disposal would prove a comparative low cost technique in ridding the user of such products after use.

Products of the present invention can be made from fabrics which are in turn created from fibers of polyvinyl alcohol. The fabric, comprised of polyvinyl homopolymer has been, in one embodiment, crystallized by postdrawing or by heat annealing or by both postdrawing and heat annealing. Preferable for use in the present invention would be a crystallized, greater than 99% saponified polyvinyl acetate. However, as specified elsewhere herein, other degrees of saponification and crystallization may be involved in providing an operable polyvinyl alcohol fiber to suit the desired purpose.

The fabric used to produce the present towels, sponges and gauzes can be configured from conventional spun yarn. However, it is preferable to process the fiber into a thermal bond, chemical bond, needle punch, wet laid, air laid or other non-woven fabric. Such processing can be accomplished using tools, methods and procedures familiar to those of ordinary skill in the art of textile manufacturing. The preferred weight of fabric for the towels, sponges and gauzes of this invention is between 15 g/yd$^2$ and 200 g/yd$^2$. Such products can be formed from a sufficient number of layers which can be bonded or sewn together.

Optionally, in a further preferred embodiment, the polyvinyl alcohol can contain from between approximately 0.1 to 5.0%(wt.), most preferably between 2 to 3%(wt.) based upon the weight of the polyvinyl alcohol, of an anti-blocking agent and/or 0.1 to 2.0%(wt.) of wetting agent based upon the weight of the polyvinyl alcohol polymer. Suitable wetting agents and blocking agents are any known in the art that can be used with polyvinyl alcohol fibers. The anti-blocking agent is used to further enhance the usability of polyvinyl alcohol in producing the present products. In particular, it is contemplated that the anti-blocking agent reduces hydrogen bonding between adjacent hydroxyl groups on separate fiber bundles. Suitable anti-blocking agents and members include, but are not limited to, silicon dioxide ($SiO_2$) polymer, talc, calcium carbonate and fumed hydrophilic $SiO_2$. Furthermore, it has been found that the incorporation of a wetting agent within the polyvinyl alcohol fiber or fabric is surprisingly useful for maximizing rate of absorbency of the article. Suitable wetting agents include, but are not limited to, fluorocarbons such as those offered by the Minnesota Mining and Manufacturing Co. sold under the trademark FC-171®.

The polymer for use herein is comprised of polyvinyl alcohol with or without acetyl groups, cross-linked or uncross-linked. The polyvinyl alcohol can be at least "partially" hydrolyzed, i.e., having greater than 80%, preferably greater than 90%, and even more preferably greater than 95%, but less than about 98% hydrolyzed acetyl groups. In a further embodiment, the polyvinyl alcohol can be "fully" hydrolyzed, i.e., has greater than 98%, and most preferably greater than 99% hydrolyzed acetyl groups.

To provide adequate mechanical strength, polyvinyl alcohol fibers should have degree of polymerization of from about 300 to about 3000, preferably of from 700 to 2000, even more preferably from 1300 to 2000 and most preferably of about 1700.

In producing polyvinyl alcohol resins for the saponification of polyvinyl acetate, impurities such as sodium acetate and sodium sulfate may be found in the resin. To provide a superior fiber, such impurities should be kept below ½% (wt.), more preferably below ¼% (wt.) of the polyvinyl alcohol resin. This can be accomplished with a methanol water rinse or extraction.

It is often desirable that the fiber be colored with pigments or dyes such as azo or anthraquinone molecules. Such pigments and dyes should be employed in an amount between approximately 0.5 to 3.0% (wt.) based upon the weight of the polymeric polyvinyl alcohol.

Subsequent to use, towels, sponges and gauzes of the present invention can be disposed of by introduction into a washing machine for from between 5 and 30 minutes at a temperature of above about 37° C. resulting in a subsequent solubilization of the polyvinyl alcohol. Preferably, the temperature of the washing machine is above 95° C. for a period of time sufficient to disinfect any potentially harmful pathogens, etc. The solution produced is suitable for disposal in the standard sewer system.

We claim:

1. An article comprising a member selected from the group consisting essentially of a towel, sponge and gauze, said article being comprised of fibers of polyvinyl alcohol resin which are selectively soluble in aqueous solutions only above approximately 37° C., said polyvinyl alcohol fibers being further characterized as having a degree of hydrolysis of at least approximately 80%, and average degree of polymerization between approximately 1300 to 2000, degree of crystallinity of at least 0.20 and a degree of orientation of at least 0.20.

2. The article of claim 1 wherein water solubility temperature for the polyvinyl alcohol fibers is greater than approximately 50° C.

3. The article of claim 1 wherein the water solubility temperature is greater than approximately 70° C.

4. The article of claim 3 wherein said polyvinyl alcohol fibers are produced by dope extrusion.

5. The article of claim 3 wherein the polyvinyl alcohol fibers are produced by melt spinning or hydrogel spinning followed by heat and stretching.

6. The article of claim 1 wherein the polyvinyl alcohol fibers have a water content of between approximately 1.5 to 15% by weight.

7. The article of claim 1 wherein said polyvinyl alcohol fibers further contain an anti-blocking agent in an amount between approximately 0.1 to 5.0% by weight.

8. The article of claim 7 wherein the anti-blocking agent is a member selected from the group consisting of silicon dioxide, talc, calcium carbonate, and fumed hydrophilic silicon dioxide.

9. The article of claim 1 wherein said polyvinyl alcohol fibers further include between approximately 0.1 to 2.0% by weight of a wetting agent.

10. The article of claim 1 which is produced by fibers of polyvinyl alcohol in the form of spun yarn, thermally bonded, chemically bonded, needle punched, wet laid, or air laid.

11. The article of claim 1 further comprising an anti-static agent.

12. The article of claim 1 further comprising a cohesion agent.

13. The article of claim 1 further comprising an anti-friction lubricant.

14. The article of claim 1 wherein said polyvinyl alcohol fibers are selectively hot water soluble only at temperatures of at least 90° C. wherein said polyvinyl alcohol is provided with a degree of hydrolysis of at least approximately 98%.

15. An article comprising a member selected from the group consisting essentially of a towel, sponge and gauze, said towel being comprised of fibers of polyvinyl alcohol resin which are selectively soluble in aqueous solutions only above approximately 37° C., said polyvinyl alcohol being further characterized as being crystallized having been produced by dope extrusion followed by heating and stretching having a degree of hydrolysis of at least 98% and a degree of polymerization between approximately 1300 to 2000.

16. A method of disposing of an article comprising a member selected from the group consisting essentially of a towel, sponge and gauze, said towel being comprised of fibers of polyvinyl alcohol resin which are selectively soluble in aqueous solutions only above approximately 37° C., said polyvinyl alcohol fibers being further characterized as having a degree of hydrolysis of greater than approximately 80%, degree of polymerization between approximately 300 to 3000, a degree of crystallinity of at least 0.20 and a degree of orientation of at least 0.20, said method comprises contacting the towel, sponge or gauze with water having a temperature above 37° C. for a period of time sufficient to dissolve the towel, sponge or gauze in the water.

* * * * *